US00PP21539P3

(12) United States Plant Patent
Griffith

(10) Patent No.: US PP21,539 P3
(45) Date of Patent: Nov. 30, 2010

(54) ***LANTANA* PLANT NAMED 'CHAPEL HILL GOLD'**

(50) Latin Name: ***Lantana* sp.**
Varietal Denomination: Chapel Hill Gold

(75) Inventor: Mark Griffith, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 204 days.

(21) Appl. No.: 12/231,672

(22) Filed: Sep. 4, 2008

(65) Prior Publication Data

US 2010/0058503 P1 Mar. 4, 2010

(51) Int. Cl.
*A01H 5/00* (2006.01)

(52) U.S. Cl. ..... Plt./227

(58) Field of Classification Search ..... Plt./227
See application file for complete search history.

(56) References Cited

U.S. PATENT DOCUMENTS

PP19,548 P2 * 12/2008 Dirr ..... Plt./227

OTHER PUBLICATIONS

*Lantana* sp 'Chapel Hill Gold' Brochure hand-out at Southern Nursery Association trade show, Aug. 7-9, 2008.

* cited by examiner

*Primary Examiner*—Wendy C. Haas
(74) *Attorney, Agent, or Firm*—Greenlee Sullivan PC

(57) ABSTRACT

A new and distinct cultivar of *Lantana* plant named 'Chapel Hill Gold', characterized by its low growing, layered and spreading growth habit; leathery, scabrous dark green foliage; continuous flowering; bright golden yellow flower buds and flowers; and cold hardiness to USDA Hardiness Zone 7.

3 Drawing Sheets

Genus and species of plant claimed: *Lantana* sp.
Variety denomination: 'Chapel Hill Gold'.

BACKGROUND OF THE INVENTION

The present invention relates to a new and distinct cultivar of *Lantana* plant, botanically known as *Lantana* sp., and hereinafter referred to by the cultivar name 'Chapel Hill Gold'.

The new *Lantana* plant originated as a naturally occurring branch mutation on *Lantana* sp. 'Chapel Hill Yellow' (Plant patent application Ser. No. 11/999,902, filed Dec. 7, 2007, which issued as U.S. Plant Pat. No. 19,548 on Dec. 2, 2008). The cultivar 'Chapel Hill Gold' originated and was discovered in a cultivated environment at Watkinsville, Ga.

Asexual reproduction of the new cultivar by stem cuttings in Watkinsville, Ga. has shown that all the unique features of this new *Lantana,* as herein described, are stable and reproduced true-to-type through successive generations of such asexual propagation.

SUMMARY OF THE INVENTION

Plants of the new cultivar 'Chapel Hill Gold' have not been observed under all possible environmental conditions. The phenotype may vary somewhat with changes in light, temperature, soil and rainfall without, however, any variance in genotype.

The following traits have been repeatedly observed and are determined to be unique characteristics of 'Chapel Hill Gold'. These characteristics in combination distinguish 'Chapel Hill Gold' as a new and distinct cultivar: 1. Low growing, layered and spreading growth habit; 2. Leathery, scabrous dark green foliage; 3. Continuous flowering; 4. Bright golden yellow flower buds and flowers; and 5. Cold hardiness to USDA Hardiness Zone 7.

Plants of the new *Lantana* 'Chapel Hill Gold' differ from plants of the parent, 'Chapel Hill Yellow', primarily in flower color, as plants of 'Chapel Hill Yellow' have pale yellow flower buds that open to medium yellow with a darker yellow-orange center.

Plants of the new *Lantana* can be compared to plants of the cultivar 'New Gold'(unpatented). However, in side-by-side comparisons conducted in Watkinsville, Ga., plants of the new *Lantana* differed from plants of the cultivar 'New Gold' in the following characteristics: 1. Plants of the new *Lantana* had darker green, thicker, more scabrous foliage than plants of the cultivar 'New Gold'; 2. Plants of the new *Lantana* had brighter golden yellow flower buds and flowers than plants of the cultivar 'New Gold'; and 3. Plants of the new *Lantana* were consistently cold hardy from year to year, whereas plants of the cultivar 'New Gold' lacked consistent cold hardiness.

BRIEF DESCRIPTION OF THE DRAWINGS

The accompanying color photographs illustrate the flower and foliage characteristics and the overall appearance of the new *Lantana,* showing the colors as true as it is reasonably possible to obtain in color reproductions of this type. Colors in the photographs may differ slightly from the color values cited in the detailed botanical description which accurately describe the colors of the new *Lantana.*

DETAILED DESCRIPTION

Figure 1:
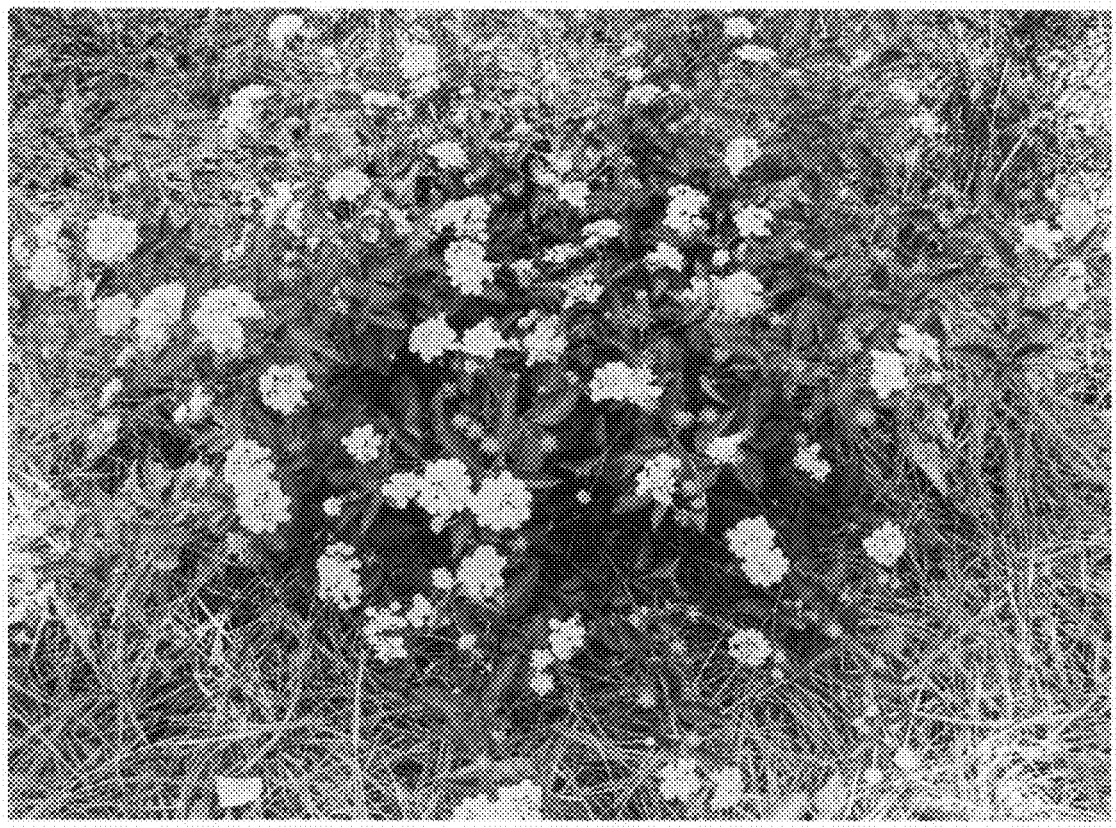
FIG. 1 illustrates the overall appearance of a mature plant of 'Chapel Hill Gold'.
Figure 2:
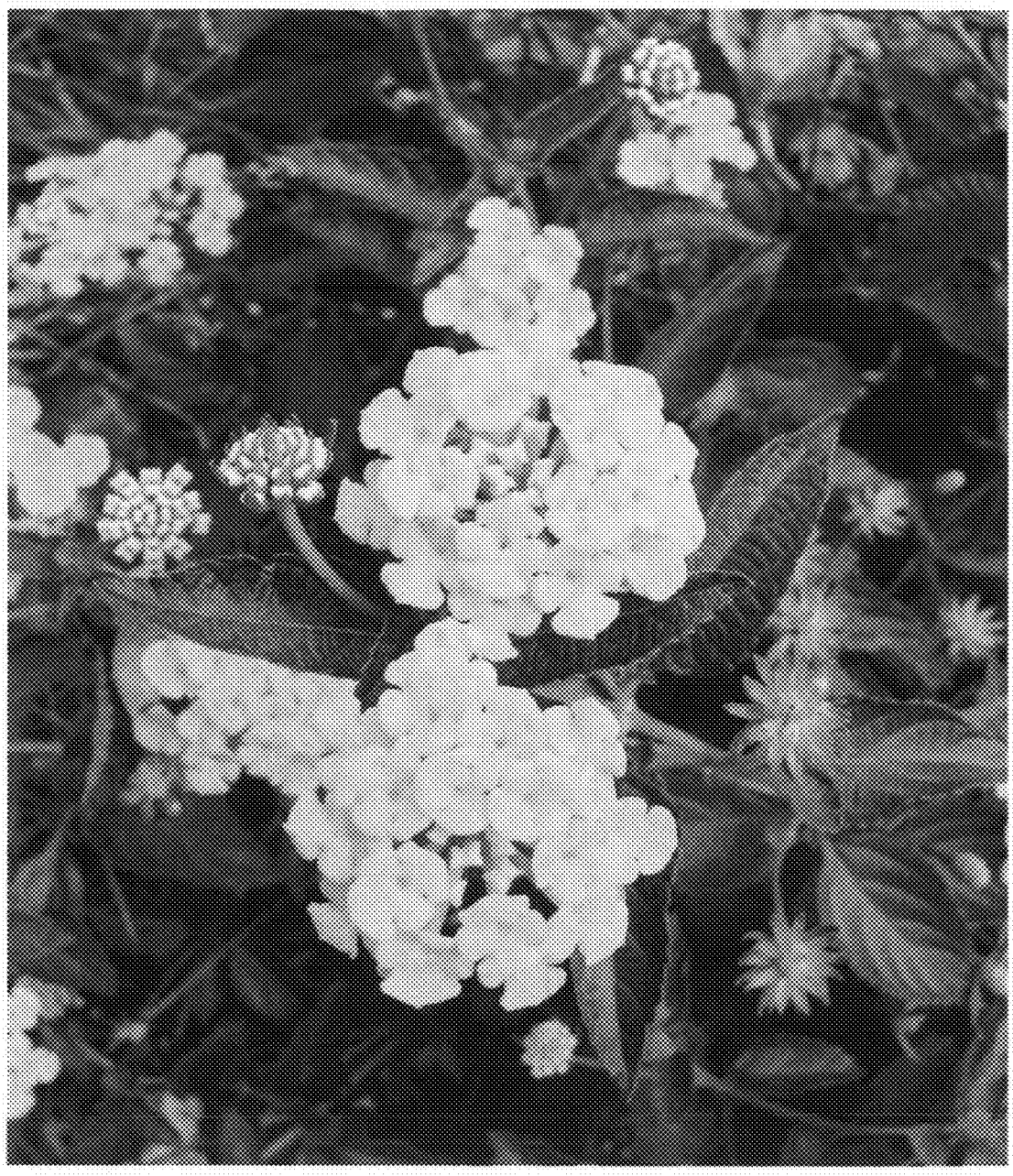
FIG. 2 illustrates a close-up view of the inflorescences of 'Chapel Hill Gold'.
Figure 3:
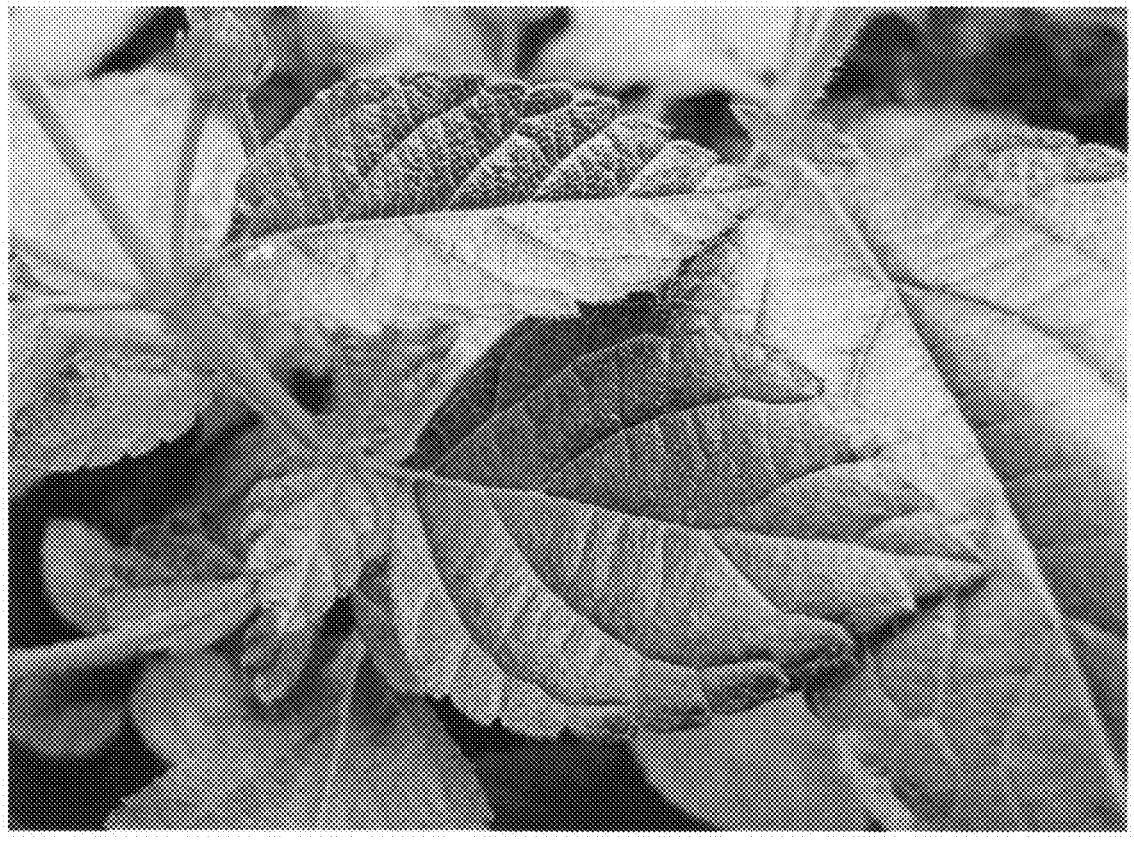
FIG. 3 illustrates a close-up view of the foliage of 'Chapel Hill Gold'.

In the following description, color references are made to The Royal Horticultural Society Colour Chart, 2001 Edition, except where general terms of ordinary dictionary significance are used. Plants used for the description were grown in 11.8 L containers under outdoor conditions in a nursery in Watkinsville, Ga. Plants were 6 months old when the description was recorded. Colors are described using The Royal Horticultural Society Colour Chart (R.H.S.).

Botanical classification: *Lantana* sp., cultivar 'Chapel Hill Gold'. Parentage:—*Lantana* sp. cultivar 'Chapel Hill Yellow' (U.S. Plant Pat. No. 19,548). Propagation: Type cutting—terminal cuttings. Time to initiate roots, summer—about 10 days at 32° C.

Plant description: Perennial flowering plant; subshrub; low growing, layered and spreading growth habit. Freely branching; two lateral branches potentially forming at every node; pinching enhances lateral branch development.

- *Root description.*—Numerous, fine, fibrous and well-branched.
- *Plant height.*—About 40 cm. Plant diameter: about 120 cm.
- *Lateral branches.*—Having a length of about 15 cm and a diameter of about 2.5 mm. Shape: Squarish.
- *Internode length.*—About 5.5 cm.
- *Strength.*—Strong, but flexible.
- *Texture.*—Coarse, pubescent.
- *Color* (*young*).—Close to 144A. Color (woody): close to 199A.

Foliage description:

- *Arrangement.*—Opposite, simple. Length: about 4 cm. Width: about 3 cm. Shape: ovate. Apex: acute. Base: cuneate. Margin: crenate.
- *Texture* (*upper surface*).—Leathery, moderately waxy, with scabrous pubescence. Texture (lower surface): rough, with hispid pubescence.
- *Venation pattern.*—Pinnate. Venation color (upper surface): close to 144A. Venation color (lower surface): close to 144A.
- *Fragrance.*—Pungent, mint-like.
- *Color in developing foliage* (*upper surface*).—Close to 137A. Color in developing foliage (lower surface): close to 138B. Color in fully expanded foliage (upper surface): close to 137A. Color in fully expanded foliage (lower surface): close to 137C.
- *Petiole length.*—About 8 mm. Petiole diameter: about 2 mm. Petiole texture, both surfaces: hispid pubescence. Petiole color (upper surface): close to 143A. Petiole color (lower surface): close to 144A.

Flower description:

- *Flower type and habit.*—Small salverform flowers arranged in axillary corymbs; flowers face mostly upward or outward. Flowers are self-cleaning. Freely flowering with potentially two inflorescences per node; typically about 27 flowers per corymb. Natural flowering season: spring until frost in the autumn; flowering is continuous. Flower longevity on the plant: about one week. Fragrance: faint, pleasant.
- *Inflorescence diameter.*—About 3.4 cm. Inflorescence height: about 1.7 cm.
- *Flower appearance.*—Flared trumpet, corolla fused, four-parted; flowers roughly rectangular in shape. Diameter: about 8 mm by 12 mm. Corolla tube length: about 1.2 cm.
- *Flower bud length.*—About 6 mm. Flower bud diameter: about 2 mm. Flower bud shape: oblong. Flower bud color: close to 17B.
- *Pedicels.*—Not observed, flowers not stalked.

Petals:

- *Arrangement/appearance.*—Single whorl of four petals, fused into flared trumpet.
- *Petal length from throat.*—About 4.5 mm for upper and lower petals and about 3 mm for lateral petals.
- *Petal width.*—Upper and lower petals are about 7 mm. Lateral petals are about 3.5 mm.
- *Petal shape.*—Spatulate to somewhat orbicular. Petal apex: obtuse. Petal base: fused. Petal margin: entire. Petal texture, upper and lower surfaces: smooth, glabrous.
- *Color of petal lobes, when opening and fully opened, upper surface.*—Close to 17A. Color of petal lobes, when opening and fully opened, lower surface: close to 17B. Color of throat: close to 17A. Color of tube: close to 17B.

Sepals:

- *Arrangement/appearance.*—One sepal per flower at the base of the corolla, leaf-like. Length is about 5 mm. Width is about 1 mm. Shape: lanceolate. Apex: acute. Margin: entire. Texture, upper and lower surface: scabrous.
- *Color, upper and lower surfaces.*—Close to 144A.

Peduncles: Length is about 4.3 cm. Diameter is about 2 mm. Angle: about 45 degrees from the stem. Strength: flexible, but strong. Color: close to 144A.

Stamens:

- *Quantity/arrangement.*—Four per flower, adnate to the inside of the corolla tube. Anther shape: oblong. Anther length: less than 1 mm. Anther color: close to 200A. Pollen amount: none observed.

Pistils:

- *Quantity.*—One per flower. Pistil length: about 2.5 mm. Stigma shape: rounded. Stigma color: close to 145A. Style color: close to 145A. Ovary color: close to 145A.

Fruit:

- *Type/appearance.*—Drupe. Shape: round. Diameter: about 5 mm. Mature color: 202A. Number per Infructescence: about 5.

Disease/pest resistance: Plants of the claimed *Lantana* variety grown in the garden have not been noted to be resistant to pathogens and pests common to *Lantana*.

Weather and temperature tolerance: Plants of the new *Lantana* variety have been observed to be tolerant to rain and wind, and have been observed to be tolerant to temperatures ranging from about 0 degrees C. to about 38 degrees C. and are hardy to about USDA Hardiness Zone 7.

I claim:

1. A new and distinct *Lantana* plant named 'Chapel Hill Gold', as illustrated and described herein.

* * * * *